United States Patent
Roche et al.

(10) Patent No.: US 6,618,143 B2
(45) Date of Patent: *Sep. 9, 2003

(54) HIGH NUMERICAL APERTURE FLOW CYTOMETER AND METHOD OF USING SAME

(75) Inventors: John W. Roche, Scarborough, ME (US); W. Peter Hansen, Canaan, NY (US); Harold C. Flynn, Jr., Scarborough, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/969,242

(22) Filed: Oct. 2, 2001

(65) Prior Publication Data

US 2002/0113965 A1 Aug. 22, 2002

Related U.S. Application Data

(63) Continuation-in-part of application No. 09/507,515, filed on Feb. 18, 2000, now Pat. No. 6,320,656.

(51) Int. Cl.[7] .................... G01N 21/00; G01N 33/48
(52) U.S. Cl. .................... 356/339; 356/343; 356/73; 436/63
(58) Field of Search .................... 356/335–343, 356/39, 73, 40; 436/63, 10, 149, 43, 54, 172, 180, 522, 523; 422/63, 67, 73, 82.08

(56) References Cited

U.S. PATENT DOCUMENTS

| | | | |
|---|---|---|---|
| 4,284,412 A | | 8/1981 | Hansen et al. |
| 4,565,448 A | * | 1/1986 | Abbott et al. ............... 359/336 |
| 4,606,636 A | * | 8/1986 | Monin et al. ............... 356/338 |
| 4,818,103 A | * | 4/1989 | Thomas et al. ............... 356/72 |
| 4,954,715 A | * | 9/1990 | Zold ............... 356/72 |

(List continued on next page.)

FOREIGN PATENT DOCUMENTS

| | | |
|---|---|---|
| WO | WO 00/49387 | 8/2000 |
| WO | WO 01/94938 A1 | 12/2001 |

OTHER PUBLICATIONS

International Search Report—dated Jan. 20, 2003.

*Primary Examiner*—Hoa Q. Pham
(74) *Attorney, Agent, or Firm*—Carter, DeLuca, Farrell & Schmidt, LLP

(57) ABSTRACT

The high numerical aperture flow cytometer of the present invention includes a flow cell and a laser input. The laser input emits a beam of light that is oriented substantially orthogonally to the flow of blood cells through the flow cell such that laser light impinges upon the blood cells as they pass through the flow cell. A portion of the beam from the laser input that impinges upon the blood cells in the flow cell is scattered at a substantially right angle to the beam of laser input ("right angle scatter"). A second portion of the beam from the laser input that impinges upon the cells in the flow cell is scattered at a much lower angle than 90°. This scatter is termed forward scatter light" and is collected on two distinct photo detectors, that represent 'forward scatter low' (FSL) which has an angle of from about 1° to about 3°, and 'forward scatter high' (FSH) which has an angle of from about 9° to about 12° from the orientation of the original beam from laser input. A third photo detector is placed in between these two forward scatter detectors, that is axial with the impinging laser light. This detector measures axial light loss, or light extinction (EXT) which is the sum of all the light that is absorbed and scattered by the blood cells. A right angle scatter light detector is oriented to receive the previously mentioned right angle scatter light. A forward scatter light detector is oriented to capture the previously mentioned forward scatter light oriented different angles from the beam of the laser input.

15 Claims, 21 Drawing Sheets

U.S. PATENT DOCUMENTS

| | | | |
|---|---|---|---|
| 5,017,497 A | * 5/1991 | Grooth et al. | 356/337 |
| 5,179,026 A | * 1/1993 | Matsuda et al. | 436/63 |
| 5,264,369 A | * 11/1993 | Sakata et al. | 436/63 |
| 5,308,772 A | * 5/1994 | Sakata et al. | 436/63 |
| 5,408,307 A | * 4/1995 | Yamamoto et al. | 356/73 |
| 5,432,601 A | * 7/1995 | Tanaka et al. | 356/246 |
| 5,467,189 A | * 11/1995 | Kreikebaum et al. | 356/336 |
| 5,631,165 A | * 5/1997 | Chupp et al. | 436/43 |
| 5,650,847 A | * 7/1997 | Mallsev et al. | 356/336 |
| 5,747,343 A | * 5/1998 | Tsuchiya et al. | 436/63 |
| 5,940,177 A | * 8/1999 | Esser et al. | 356/338 |
| 6,320,656 B1 | * 11/2001 | Ferrante et al. | 356/339 |

* cited by examiner

HIGH NUMERICAL APERTURE FLOW CYTOMETER AND METHOD OF USING SAME

This application is a continuation-in-part application of copending U.S. patent application Ser. No. 09/507,515, filed on Feb. 18, 2000, now U.S. Pat. No. 6,320,656, the entire text and figures of which are hereby incorporated by reference.

FIELD OF THE INVENTION

The present invention relates to particle discrimination by light scattering, and more particularly to a flow cytometer and method therefore that discriminates particles employing a high numerical aperture. Numerical aperture is defined as the refractive index of the medium through which light is collected multiplied by the sine value of one-half of the angle of light collection.

BACKGROUND OF THE INVENTION

The discrimination of particles is useful in numerous clinical assays including ascertaining the types and numerical quantity of cells in blood, ascertaining invasive particles in a fluid sample, such as bacteria and virus, and quantifying the density and volume of cells in a fluid sample.

One method of the above is disclosed in U.S. Pat. No. 5,017,497 issued to de Grooth et al. Referring to FIG. 1, the '497 Patent discloses a flow cell 2 through which cells from, for example, blood or the like, flow substantially one by one therethrough. A laser input 4 emits a polarized beam of laser light that is oriented substantially orthogonally to the flow of blood cell through flow cell 2 such that the polarized laser light impinges upon the blood cells as they pass through flow cell 2. By "polarized" it is meant that the plane of the electric field oscillation of the laser light is uniform. An optical lens 6 has an numerical aperture of 0.6 which limits the cone of scattered light from the blood cells that can be collected to 72° or less, and practically to 50° as disclosed in the '497 Patent. The central axis of the cone of lens 6 is 90° to both the path of the polarized laser light and the flow of blood cells through flow cell 2. The scattered light emanating from lens 6 is collimated in a manner known in the art. The scattered light now has a mixed polarization that is characteristic of the cell type. The light next passes through a beam splitter 8 that divides the light into two separate beams. A first light beam, substantially concentric with the light beam that originally emanated from lens 6, passes through first polarization analyzer 10. Polarization analyzer 10 is configured to pass therethrough only polarized light having a vector the same as the original laser light. The second beam emanating from beam splitter 8 is oriented substantially perpendicular to the orientation of the first beam emanating from beam splitter 8. This second beam enters second polarization analyzer 12. Second polarization analyzer 12 is configured to pass therethrough only light having a polarization vector substantially orthogonal to the polarization vector of the other beam from beam splitter 8 that passed through first polarization analyzer 10. The beams that pass through first polarization analyzer 10 and second polarization 12 enter polarized detector 14 and depolarized light detector 16, respectively. The ratio of the outputs of polarized light detector 14 and depolarized light detector 16, based on intensity, provide the depolarization ratio.

As shown in FIG. 4 eosinophils, a subset of leukocytes (white blood cells), depolarize the right angle of scattered light quantified by the above configuration to a greater degree than other leukocytes. FIG. 4 is a graphical representation having the output of polarized light detector 14 as one axis and the output of depolarized light detector 16 as the axis. While the above invention does provide some useful data regarding leukocytes, and more specifically eosinophils, as shown in FIGS. 6B, 7B, 8B and 9B, the cluster points within the eosinophil cluster (the cluster points above the angled threshold line on the graphical representation having "DEPOL" as one axis and "ORTHAGONAL" as the other axis) are quite condensed. The dense nature of the points within the eosinophil cluster results in difficulty for the computer software programs that ascertain and identify clusters to accurately identify eosinophil clusters. Additionally, this prior art configuration requires expensive optical devices such as photo multiplier tubes, and lens 6, first polarization amplifier 10 and second polarization amplifier 12.

The prior art as indicated in the '497 Patent is unable to distinguish eosinophils without utilizing polarized and depolarized light methods, because the cone of light collected is 72° or less, based on the numerical aperture of the light collection lens, and more practically 50°, based on the number of optical elements that are used. These optical elements, such as beam splitter 8, polarization analyzers 10 and 12, and light detectors 14 and 16, contribute to reducing the effective light collection of the system is substantially less that 72°, and to more practically, 50°.

Copending U.S. patent application Ser. No. 09/507,515 discloses a device and method for distinguishing eosinophils in a sample of blood cells. The device uses a right angle scatter light detector that is effective to collect a cone of unfiltered right angle scattered light of at least 100° and convert the collected right angle scattered light into a right angle scattered light signal. This signal is processed by the device to distinguish eosinophils from other leukocytes in the sample on the basis of the right angle scattered light signal.

While the device described in the '515 application is capable of detecting eosinophils using unfiltered right angle scattered light, its properties create problems for the economical production of the device. Mechanically, providing a solid mounting scheme to keep right angle scatter detector 22 in place at a very small distance to flow cell 18 is difficult to design, and more difficult to manufacture. Also, minimizing the distance from right angle detector 22 to pre-amplifier 26 is essential to eliminate electrical noise that would otherwise be picked up by the leads of the right angle photo detector 22.

A need thus exists for a flow cytometer apparatus and related method in which the cell cluster points are less dense for ease of characterization of the different cell clusters. A need also exists for the above apparatus and method which has fewer and less expensive components, and which is easy and economical to manufacture.

SUMMARY OF THE INVENTION

The lens-less light collection flow cytometer of the present invention includes a flow cell and a laser input. The laser input emits a beam of light that is oriented substantially orthogonally to the flow of blood cells through the flow cell such that laser light impinges upon the blood cells as they pass through the flow cell. Unlike the prior art, the laser light emitted by the laser input need not be polarized for analysis of the cells according to the present invention. A portion of the beam from the laser input that impinges upon the blood cells in the flow cell is scattered at a substantially right angle to the beam of laser input ("right angle scatter light"). A second portion of the beam from the laser input that impinges upon the cells in the flow cell is scattered at a much lower angle than 90°. This scatter is termed "forward scatter light" and is collected on two distinct photo detectors. The first detector represents 'forward scatter low' (FSL), i.e., forward scatter light which has an angle of from about 1° to about 3° relative to the laser beam input. A second detector represents 'forward scatter high' (FSH), i.e., forward scatter light which has an angle of from about 9° to about 12° relative to the laser beam input. A third photo detector, axial with the impinging laser light, is placed in between these two forward scatter detectors. This detector measures axial light loss, or light extinction (EXT), which is the sum of all the light that is absorbed and scattered by the blood cells. A right angle scatter light detector is oriented to receive the previously mentioned right angle scatter light. The right angle scatter light detector is preferably located about 2 millimeters from the blood cells in the flow cell. An important aspect of the present invention is that, at the distance of about 2 millimeters from the blood cells, the right angle scatter light detector collects a cone of scattered light of at least 100° or greater, and preferably 130° or greater. It is this larger light cone value over the prior art light cone of about 50° in practice, and no greater then 72° in theory, that results in the greater cluster separation in the present invention due to the larger signal gathered. In contrast, the smaller 50° cone of the prior art results in missed signals and lesser cluster separation.

The maximum 72° cone of the prior art is mathematically limited to the numerical aperture of the initial light collection lens 6. The numerical aperture for the prior art total optical system shown in FIG. 1 is much lower, because each optical element reduces the numerical aperture of the total optical system. In contrast, the apparent numerical aperture of a lensless light detection system is equal to the numerical aperture of the total optical system. When a lens less optical system is employed, a ~72° cone angle produces cluster separations that are not apparent in the prior art. Thus, a lens less light collection system may be used in a flow cytometer, which has a much lower numerical aperture, but maintains cluster separation of eosinophils. The advantage of this device is that a lower numerical aperture system can be produced more efficiently and more reproducibly than the prior art devices, because there is more working distance to place components so that the photodetector is held at the proper distance from the flow cell. Additionally, this extra working distance allows for the detector to be mounted on a printed circuit board, which reduces electronic noise, improving the overall signal-to-noise ratio of the opto-electrical system.

A forward light detector array is oriented to capture the previously mentioned forward scatter low, forward scatter high, and axial light, from the beam of the laser input.

In one embodiment of the present invention, both a right angle scatter light detector and any of the three forward light detectors are employed in order to produce a 2-dimensional cytogram. However, it should be noted that in another embodiment of the present invention, only a right angle scatter light detector is employed, forward light detector is not employed, and characterization of eosinophils is possible.

BRIEF DESCRIPTION OF THE DRAWINGS

These and other objects and features of the invention will become more fully apparent when the following detailed description of the invention is read in conjunction with the accompanying drawings.

DETAILED DESCRIPTION OF THE PREFERRED EMBODIMENTS

Figure 2:
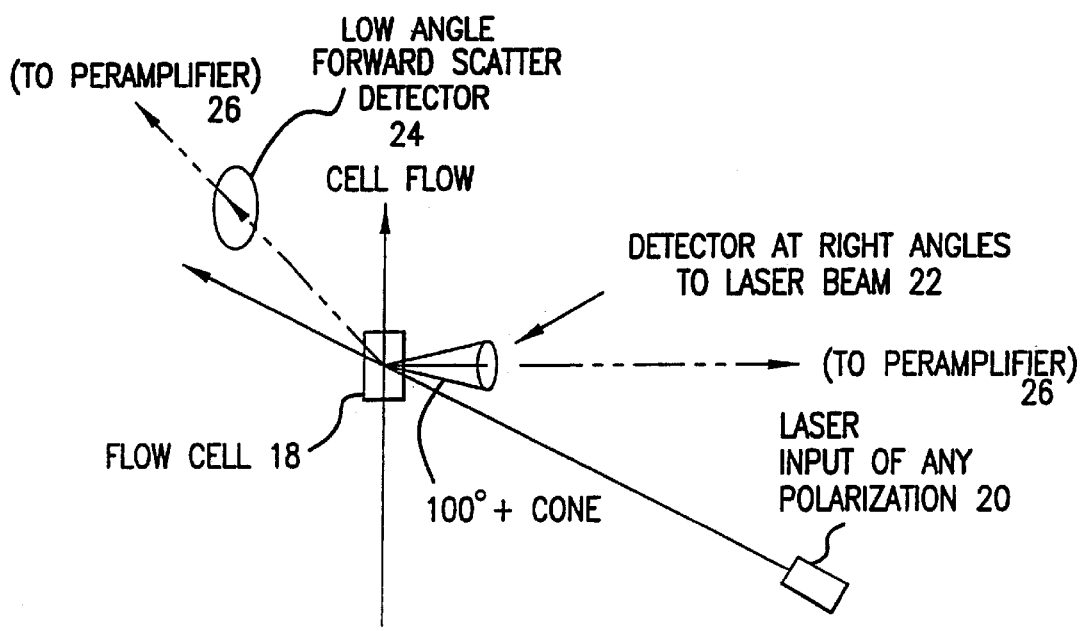
FIG. 2 is a schematic representation of the electro-optical components of the present invention.

Referring to FIG. 2, the high numerical aperture flow cytometer of the present invention includes a flow cell 18, which is preferably a quartz flow cell manufactured by Hellma GmbH and Co (Mullheim/Baden, Germany). Preferably flow cell 18 has a flow length of about 1 centimeter and a cross section of 4 millimeter by 4 millimeter. Cells from, for example, blood or the like, flow substantially one by one through flow cell 18 during analysis. Laser input 20 emits a beam of light that is oriented substantially orthogonally to the flow of blood cells through flow cell 18 such that laser light impinges upon the blood cells as they pass through flow cell 18. Unlike the prior art, the laser light emitted by laser input 20 need not be polarized for analysis of the cells according to the present invention. Laser input 20 maybe for example a 635 manometer semiconductor diode laser with an output power of 10 milliwatts, model No. HL6320G manufactured by Hitachi and available from Coherent, Inc., Auburn, Calif. A portion of the beam from laser input 20 that impinges upon the blood cells in flow cell 18 is scattered at a substantially right angle to the beam of laser input 20 ("right angle scatter light"). A second portion of the beam from laser input 20 that impinges upon the cells in flow cell 18 is scattered at a much lower angle than 90°. This scatter is termed "forward scatter light" and is collected on two distinct photo detectors, one of which represents 'forward scatter low' (FSL) which has an angle of from about 1° to about 3°, and the other of which represents 'forward scatter high' (FSH) which has an angle of from about 9° to about 12°, each measured from the orientation of the original laser beam input. A third photo detector is placed between these two forward scatter detectors, that is, axial with the impinging laser light. This detector measures axial light loss, or light extinction (EXT), which is the sum of all the light that is absorbed and scattered by the blood cells. Right angle scatter light detector 22 is oriented to receive the previously mentioned right angle scatter light. Right angle scatter light detector is preferably located about 2 millimeters from the blood cells in the flow cell 18.

Figure 11:
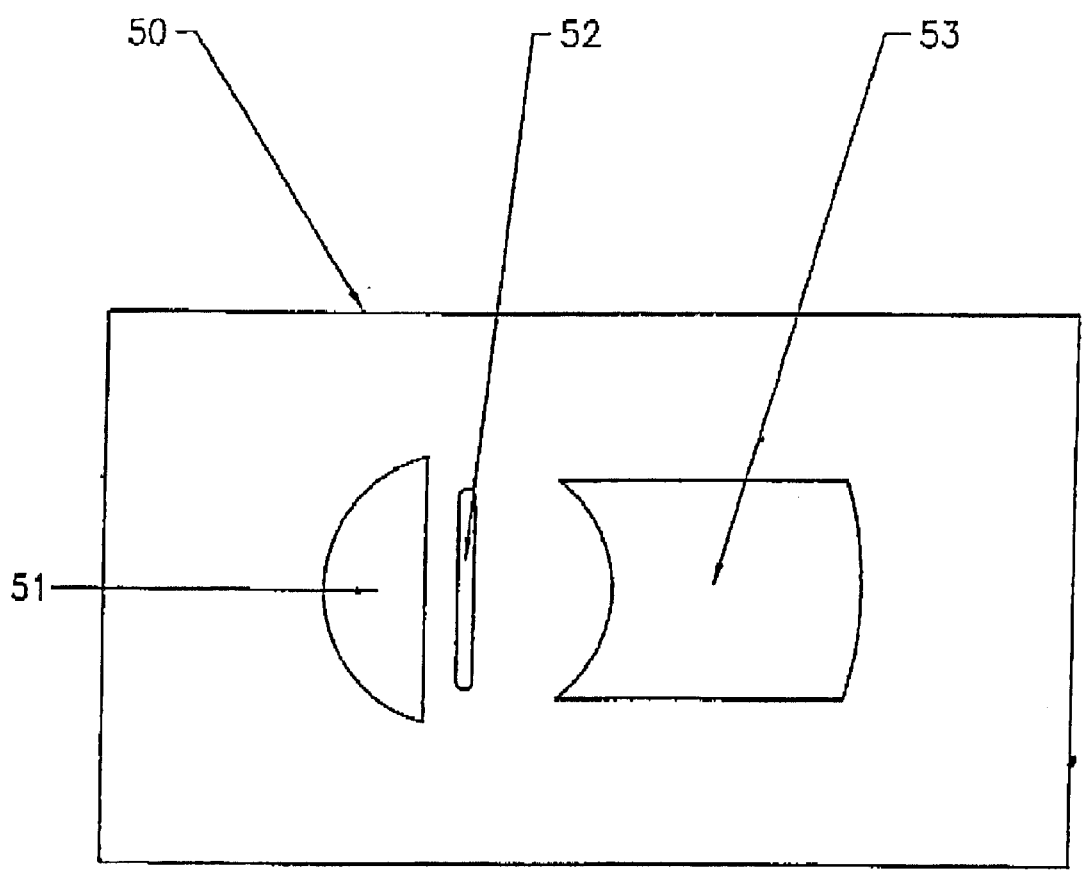
FIG. 11 is a schematic illustration of a Mie mask used in a photodetector of a preferred embodiment of the present invention.

Forward scatter light detector 24 is oriented to capture the previously mentioned axial light loss and forward scatter light, i.e., 'forward scatter low' (FSL) and 'forward scatter high' (FSH). One embodiment of light detector 24 is shown in FIG. 11, where custom detector array 50 is axial with laser input 20. Custom detector array 50 has three distinct photo detectors, or apertures. Aperture 52 collects axial light loss or extinction, aperture 51 collects forward scatter low, and aperture 53 collects forward scatter high.

In one embodiment of the present invention, both right angle scatter light detector 22 and any of the signals from forward scatter light detector 24 are employed in order to produce a 2-dimensional cytogram. However, it should be noted that in another embodiment of the present invention, only right angle scatter light detector 22 is employed, forward scatter light detector 24 is not employed, and characterization of eosinophils is possible.

To implement a mounting scheme that would allow for a robust detector mount that includes right angle photo detector 22 and a printed circuit board that represent preamplifier 26, slightly more space was needed between flow cell 18 and right angle detector 22. This effectively would cut down the cone of light collection from ~100°, to a lower value. To determine how far from flow cell 18, detector 22 could be placed, detector 22 was placed on a moveable optical positioning stage, so that it could be moved to various distances from flow cell 18, and thus changing the cone of light that it could collect.

Figure 10:
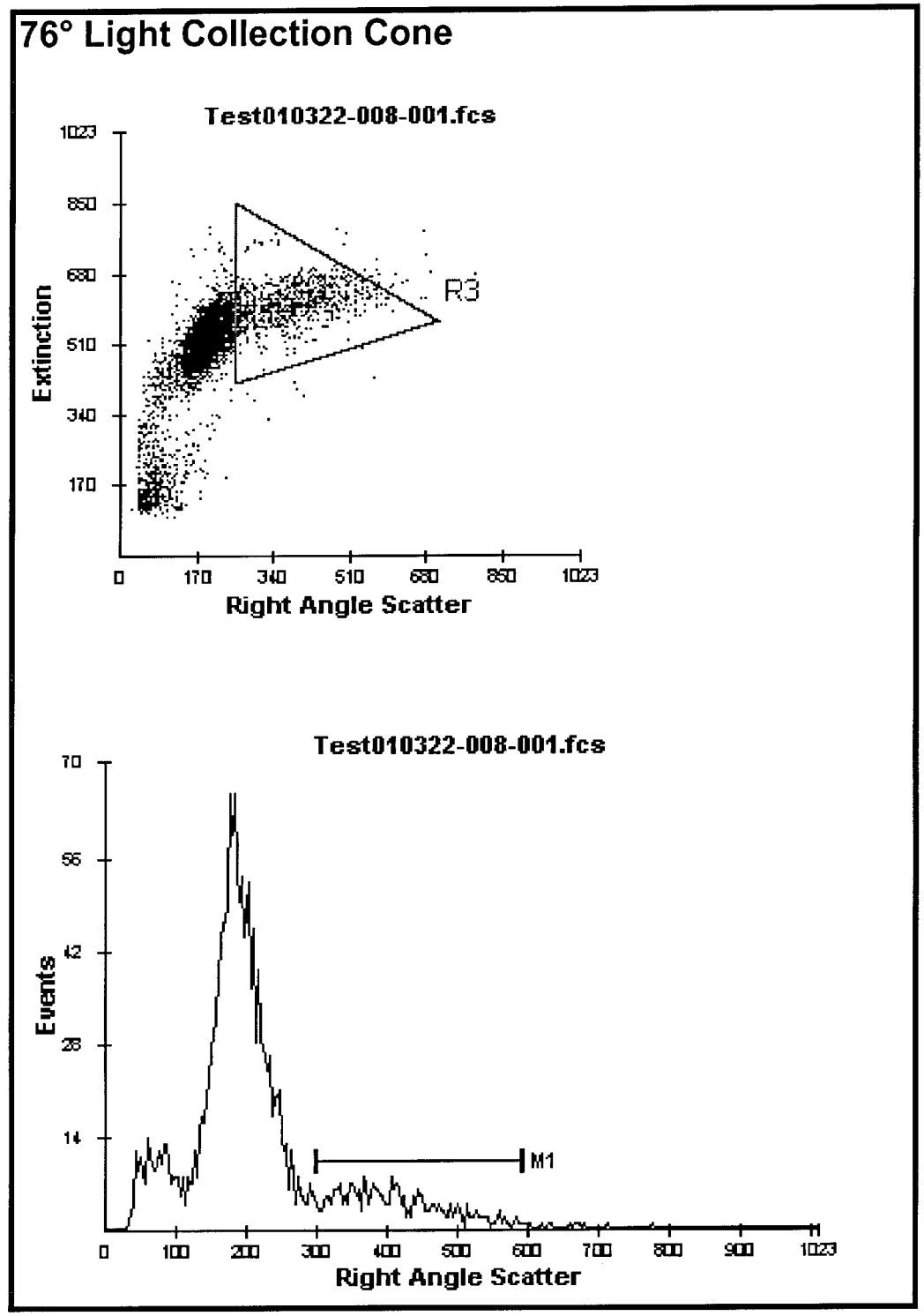
FIG. 10A is a graphical representation of feline eosinophil data obtained using the device of the present invention, showing a cone of right angle scattered light at 76°.
FIG. 10B is a graphical representation of feline eosinophil data obtained using the device of the present invention, showing a cone of right angle scattered light at 66°.
FIG. 10C is a graphical representation of feline eosinophil data obtained using the device of the present invention, showing a cone of right angle scattered light at 58°.
FIG. 10D is a graphical representation of feline eosinophil data obtained using the device of the present invention, showing a cone of right angle scattered light at 53°.
FIG. 10E is a graphical representation of feline eosinophil data obtained using the device of the present invention, showing a cone of right angle scattered light at 46°.
FIG. 10F is a graphical representation of feline eosinophil data obtained using the device of the present invention, showing a cone of right angle scattered light at 42°.
FIG. 10G is a graphical representation of feline eosinophil data obtained using the device of the present invention, showing a cone of right angle scattered light at 42°, as in FIG. 10F, but with higher gain to position the mean neutrophil cluster in the same absolute position as in FIG. 10A.
FIG. 10H is a graphically representation of feline eosinophils employing the prior art.
Figure 10:
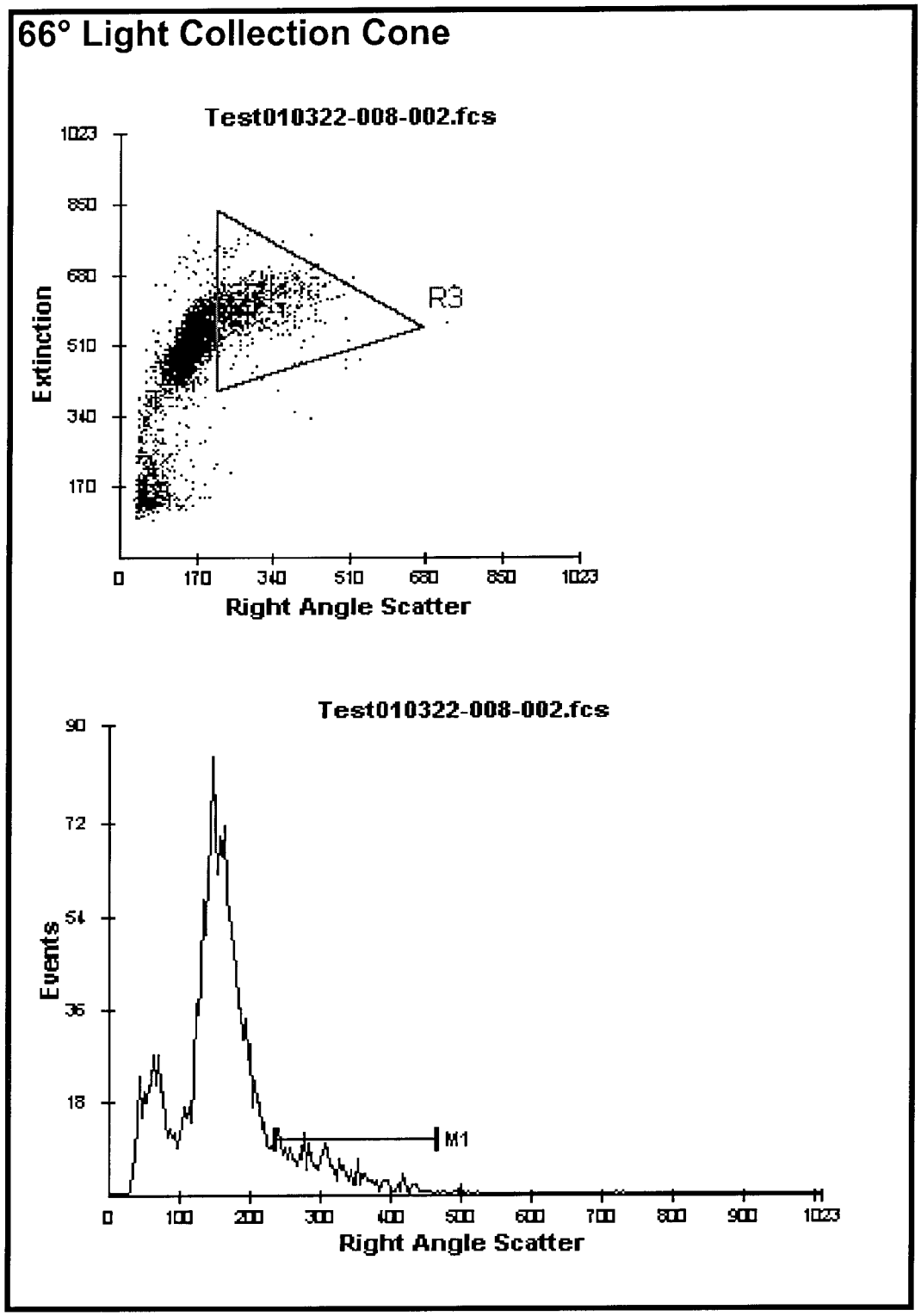
Figure 10:
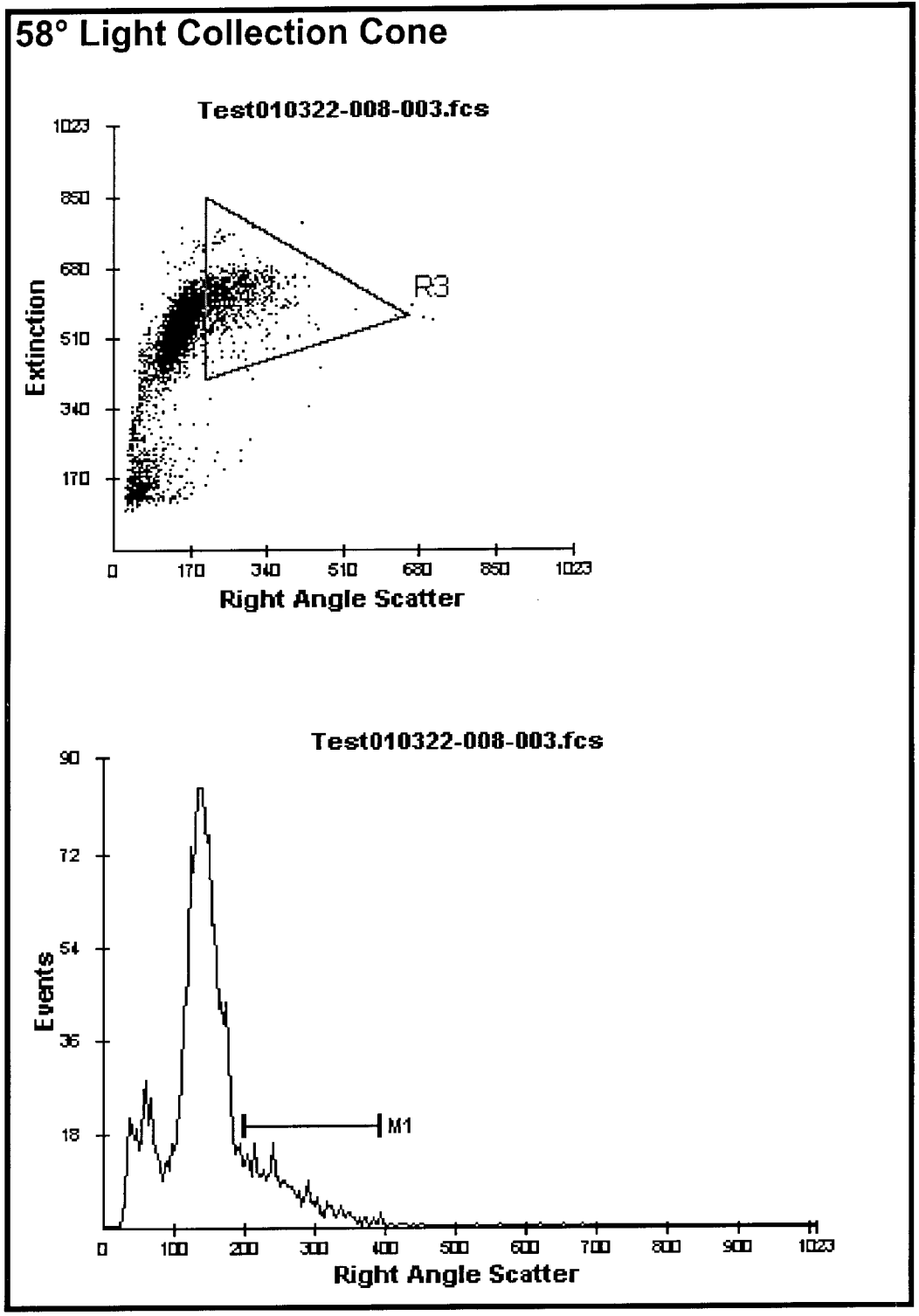
Figure 10:
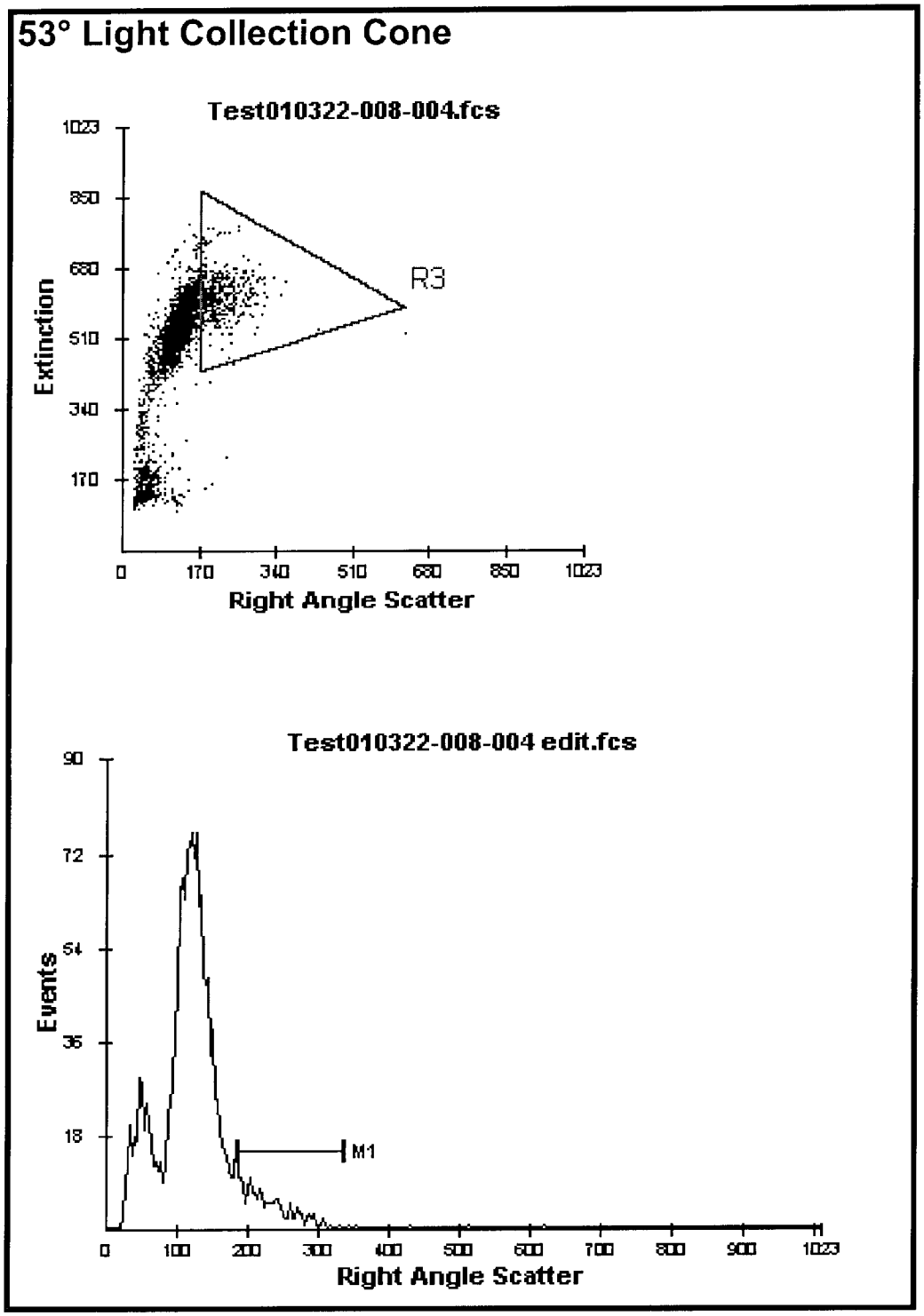
Figure 10:
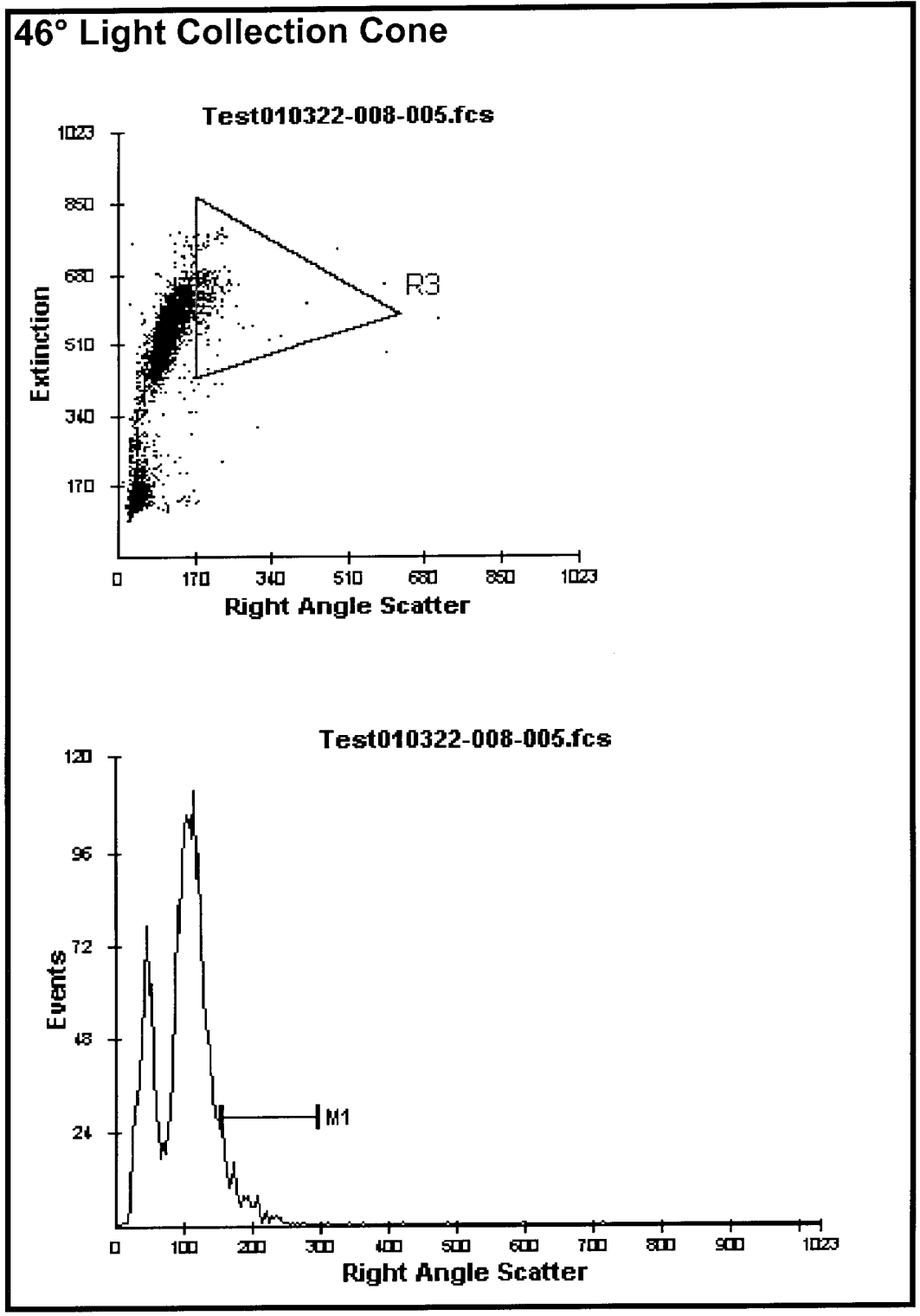
Figure 10:
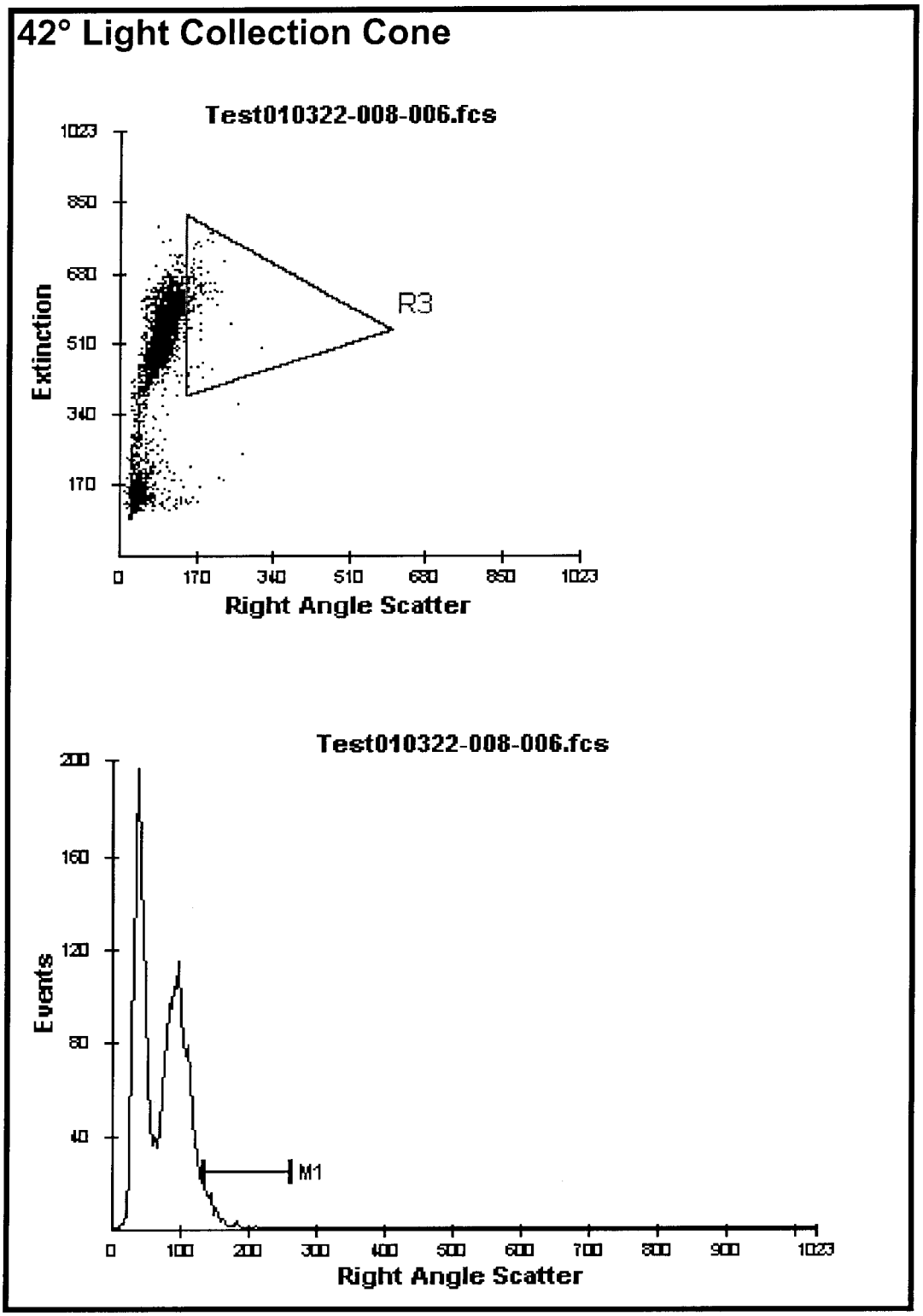
Figure 10:
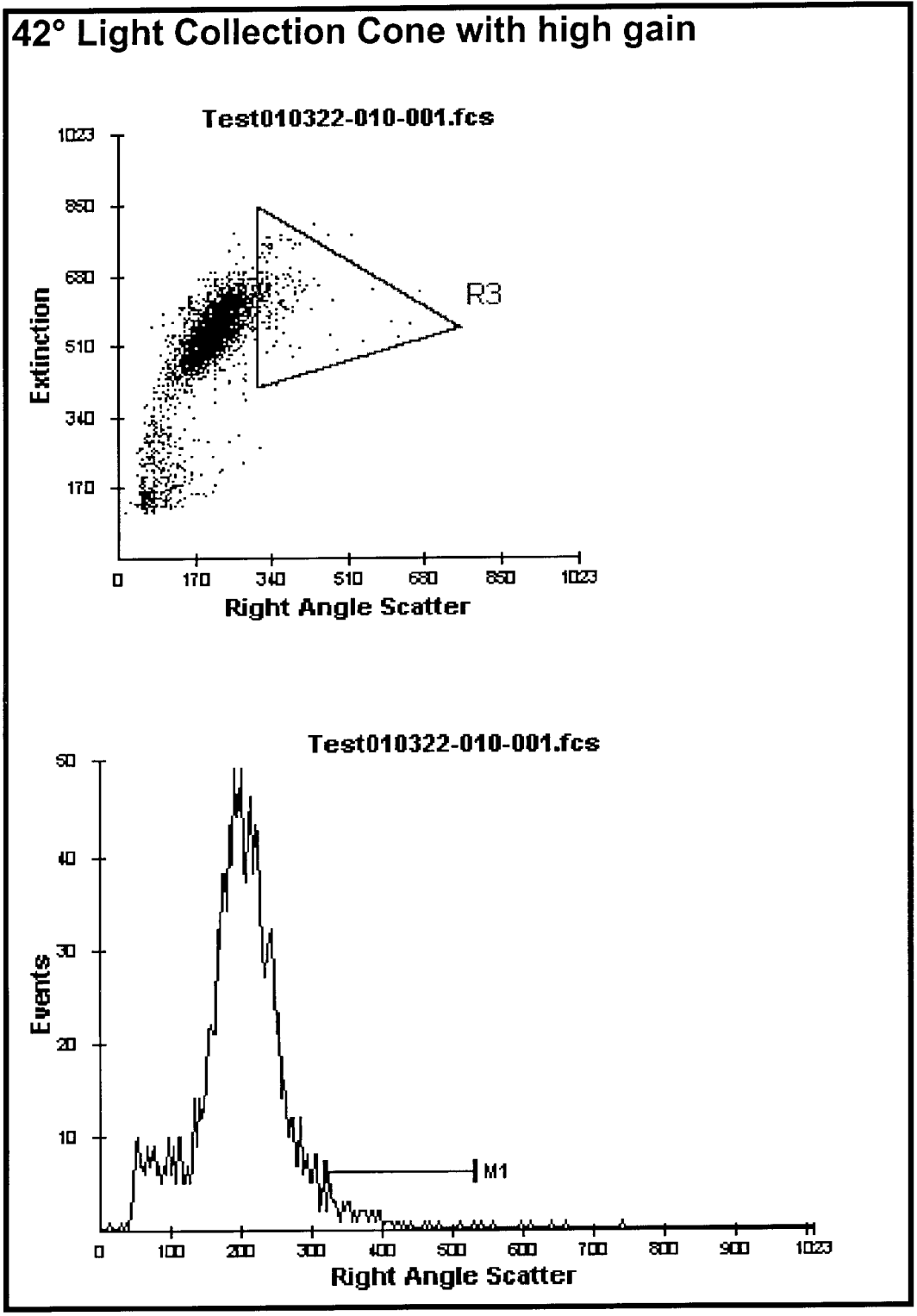
Figure 10:
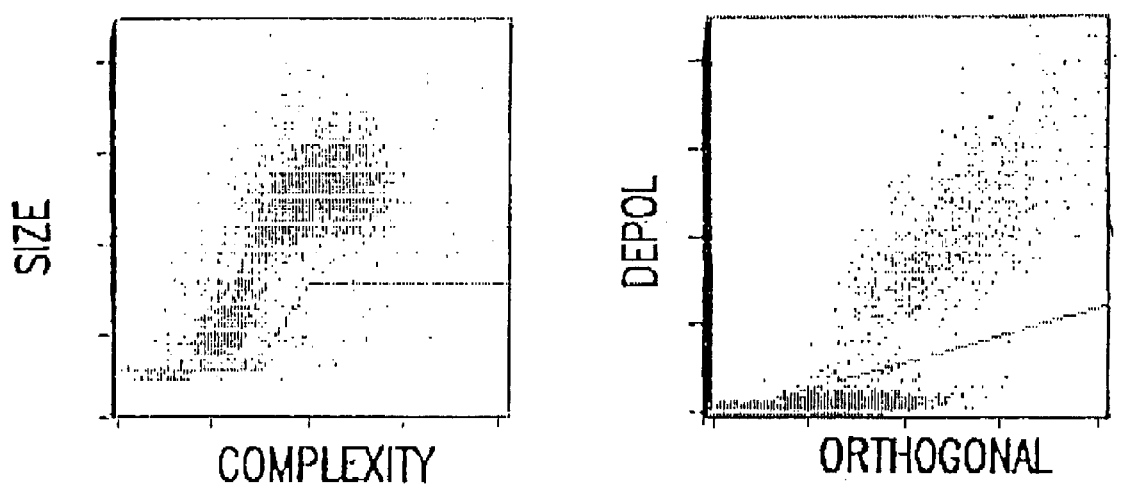

Indications form the prior art were that values of greater than 72° needed to be achieved to show results that are representative of FIGS. 6 through 9. FIG. 10 shows different cone angles of light collection, utilizing the same blood sample. The results of the separation experiments are shown in Table 1. For comparison purposes, the percentage of eosinophils obtained using the device of the '497 patent was 16.0%.

TABLE 1

| FIGURE | Cone Angle | Eosinophils Separation Quality | Eosinophil Percentage |
|---|---|---|---|
| 10A | 76° | Excellent | 16.5% |
| 10B | 66° | Good | 15.9% |
| 10C | 58° | Good | 13.7% |
| 10D | 53° | Fair | 10.5% |
| 10E | 46° | Poor | 3.1% |
| 10F | 42° | Poor | 2.5% |
| 10G | 42° (high gain) | Poor | 3.5% |

While the electro-optical elements of FIG. 2 have been described above using specific components, it will readily be apparent to one skilled in the art that different components can be employed to achieve the desired results described above. More specifically, reference is made to Practical Flow Cytometry $3^{rd}$ Ed. 1995 by Howard M. Shapiro, Wiley-Liss Publisher, ISBN No. 0-471-30376-3, which is incorporated herein by reference.

Figure 3:
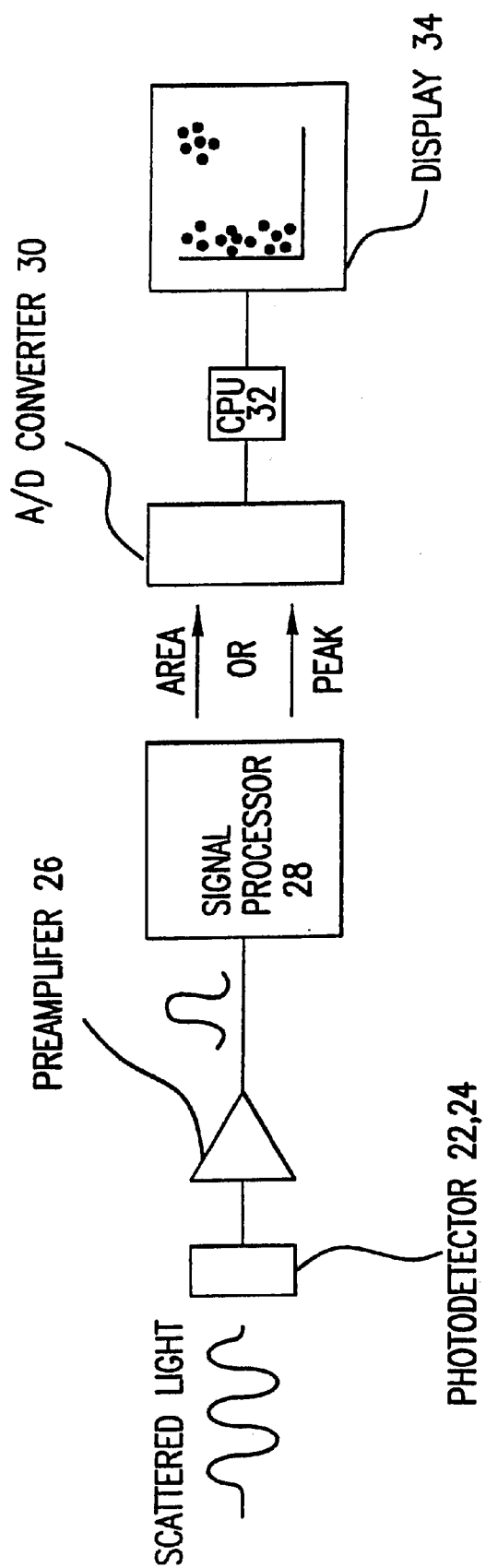
FIG. 3 is a block diagram of the electronic processing components of the present invention.
Figure 4:
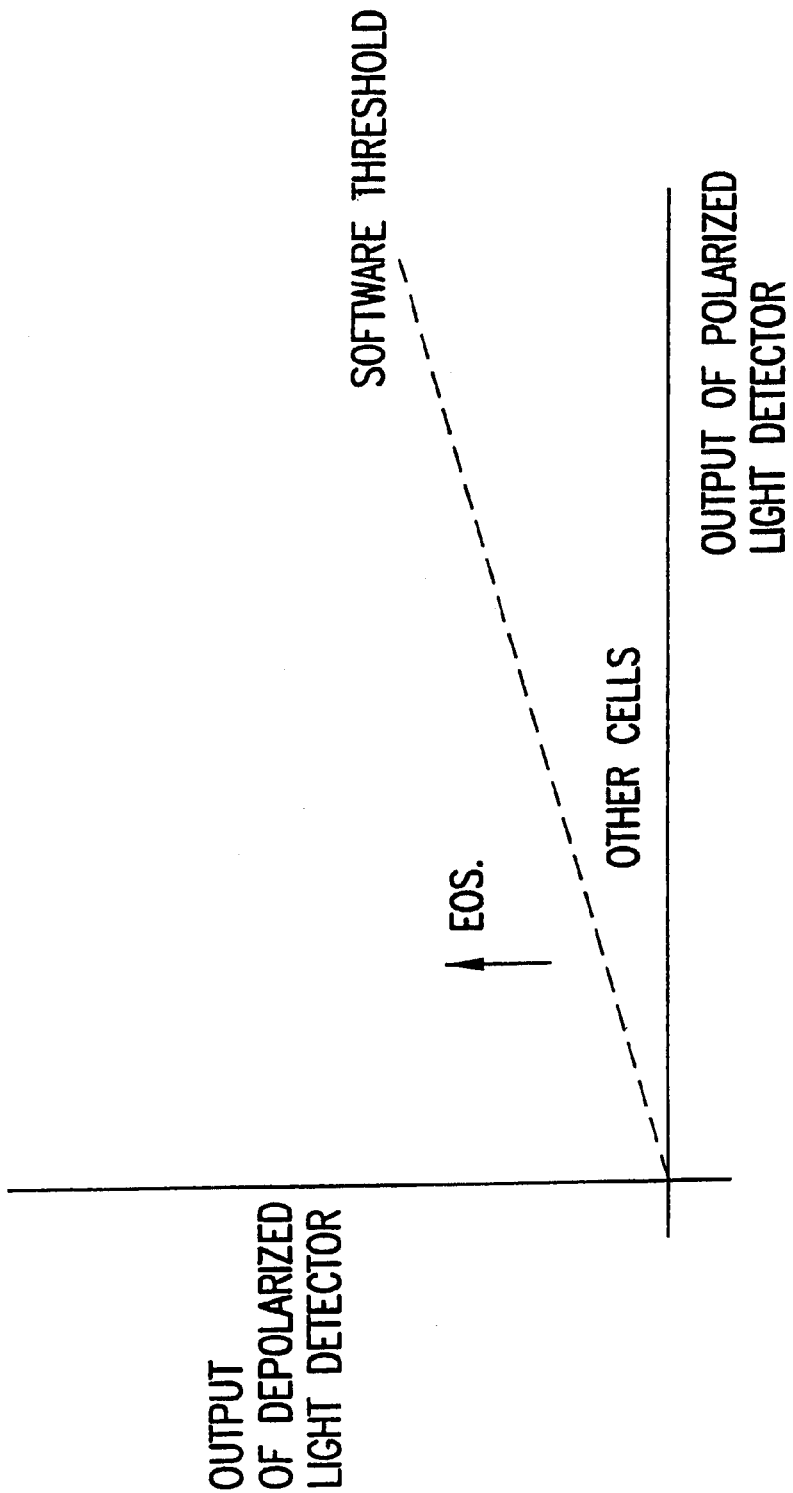
FIG. 4 is a graphical representation of the separation of eosinophils and other white blood cell components based on light scatter in the prior art.

Referring to FIG. 3, the electrical outputs from right angle scatter light detector 22 and low angle forward scatter light detector 24, which may be in voltage or current form, for example, are amplified by preamplifier 26 and then sent to signal processor 28. Signal processor 28 measures the area under the voltage or current curve, or measures the peak of the voltage or current curve, received from right angle light scatter detector 22 and/or low angle forward scatter light detector 24. The data from signal processor 28 is converted by analog to digital converter 30. The digital data is next processed by central processing unit 32 based on software programs to display the data in graphical representation on display 34. It will be readily apparent to those skilled in the art that the signal amplification, processing, conversion and display can be accomplished by many well known methods, including but not limited to those disclosed in Practical Flow Cytometry $3^{rd}$ Ed. by Howard M. Shapiro, 1995 Wiley-Liss Publishers, ISBN No. 0-471-30376-3, incorporated herein by reference.

Figure 5:
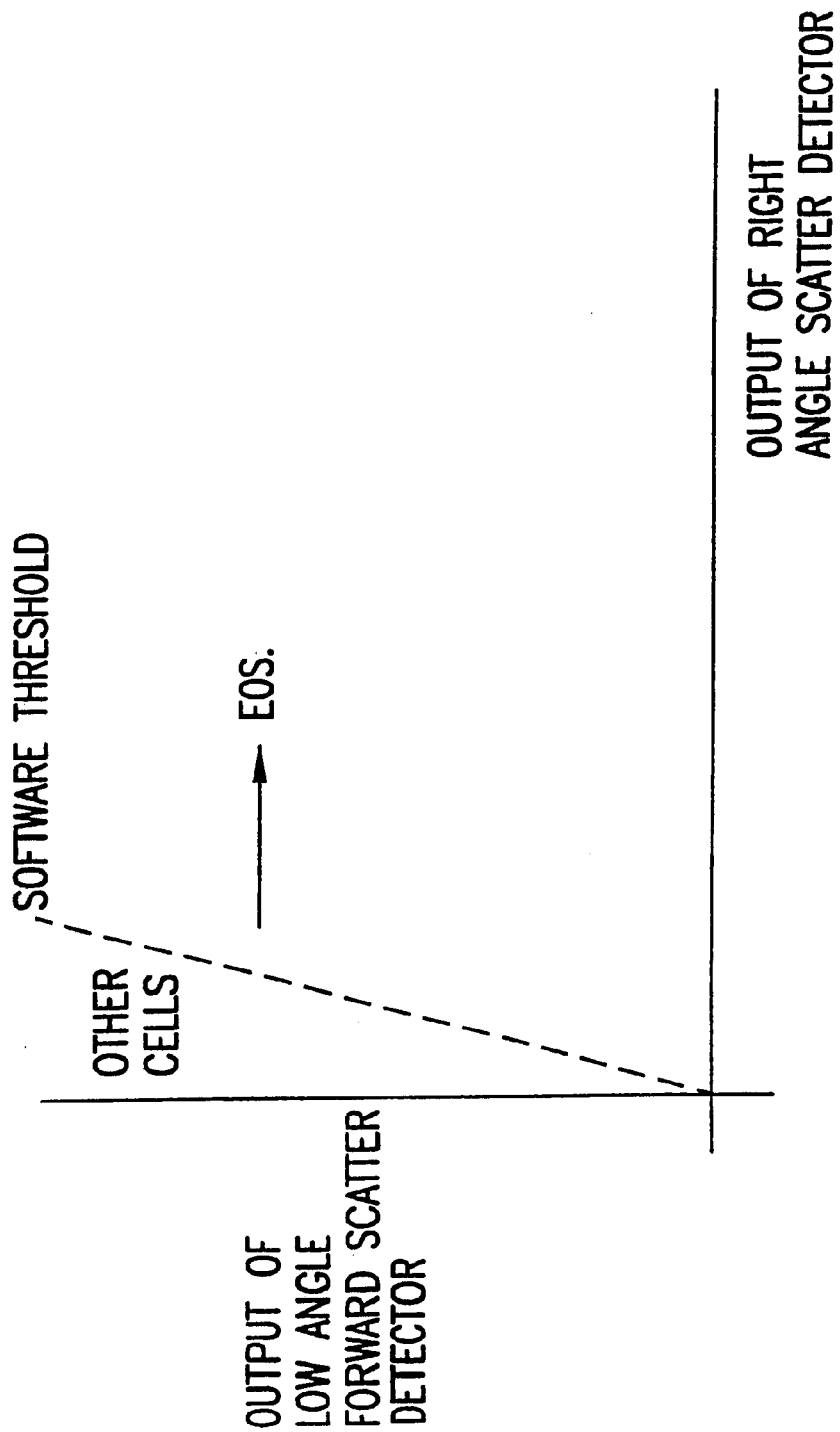
FIG. 5 is a graphical representation of the separation of eosinophils and other white blood cell components based on light scatter in the present invention.
Figure 6A:
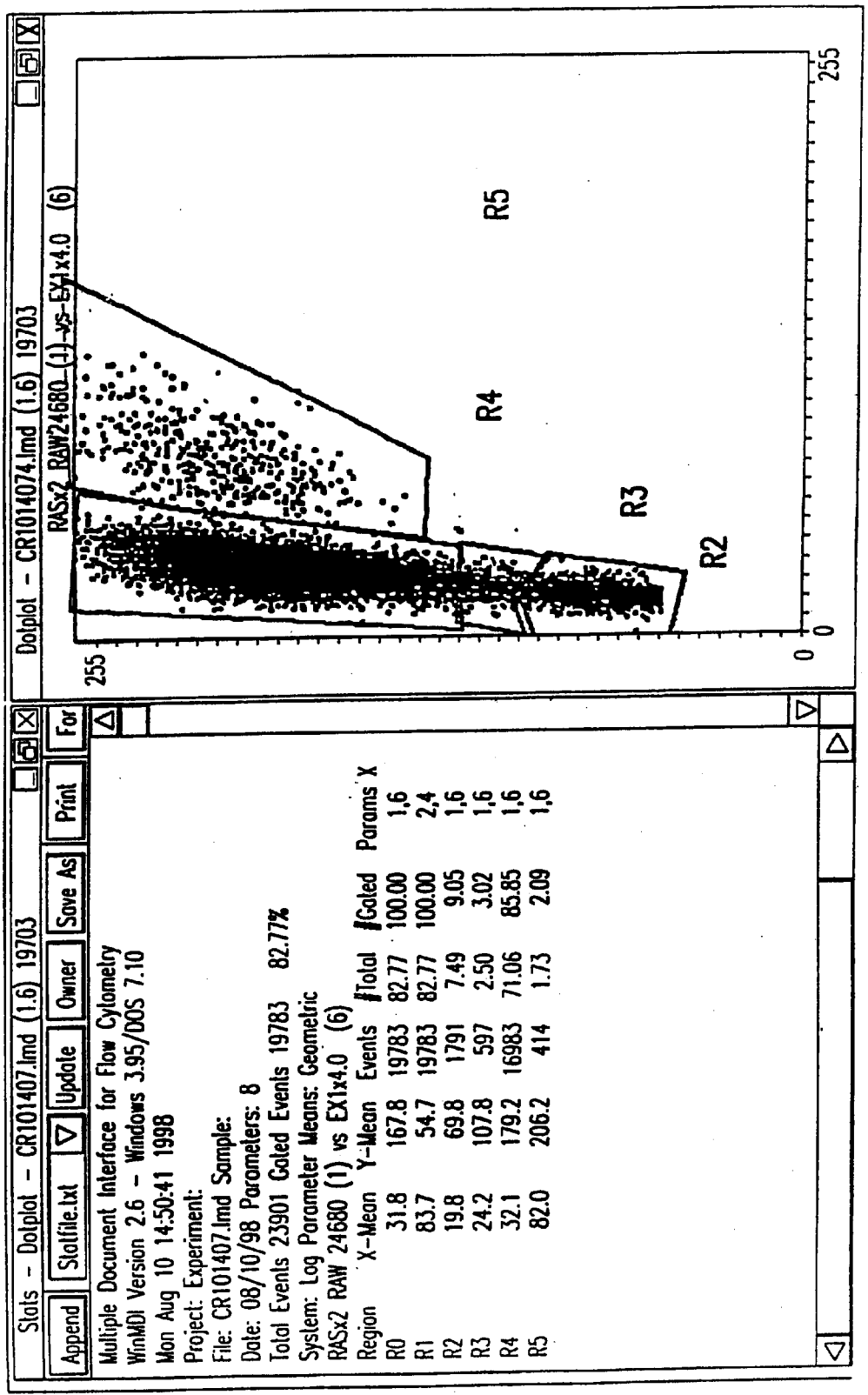
FIG. 6A is a graphical representation of 2% canine eosinophil data employing the prior art.
Figure 6B:
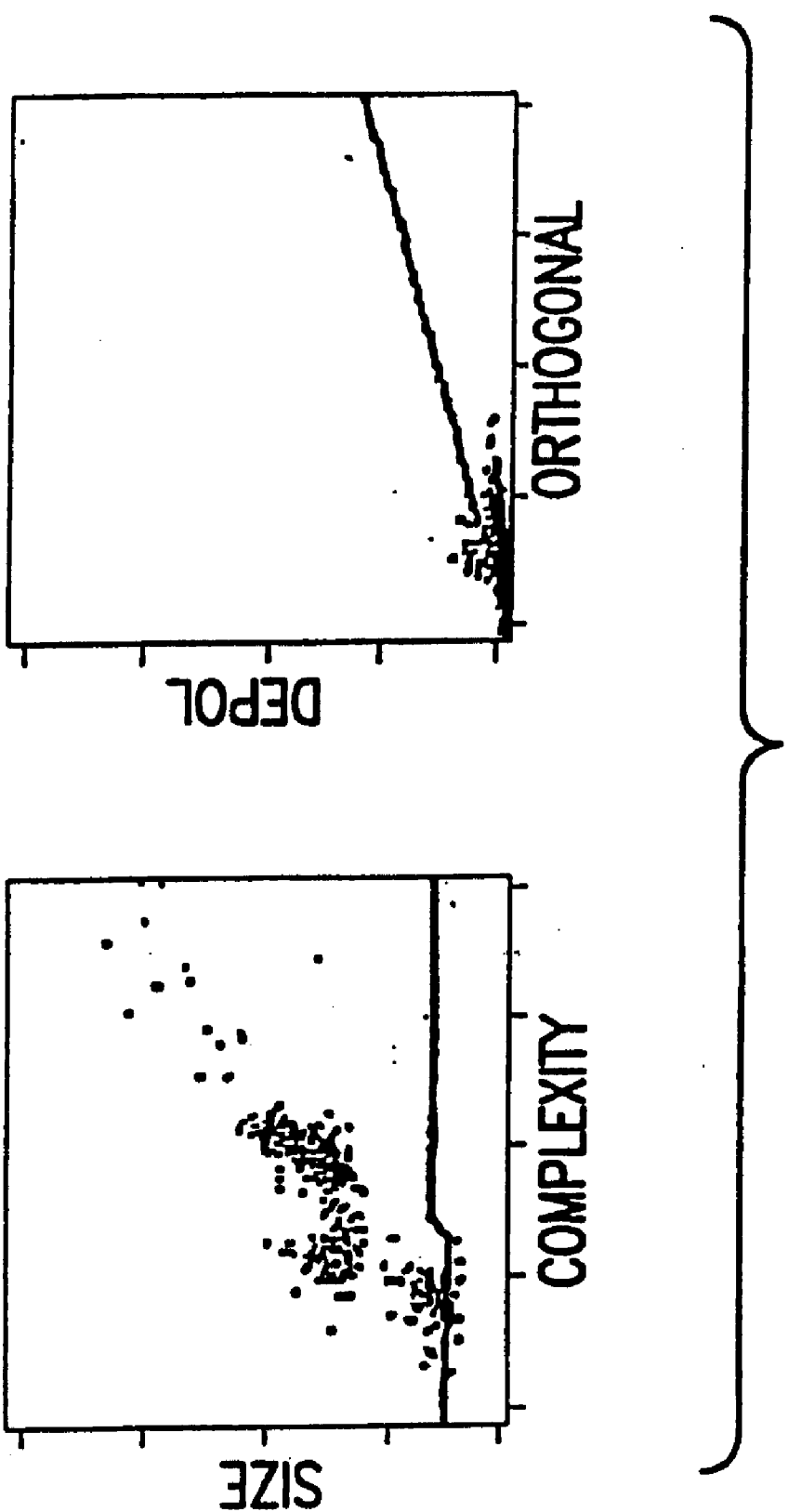
FIG. 6B is a graphical representation of 2% canine eosinophil data employing the present invention.
Figure 7A:
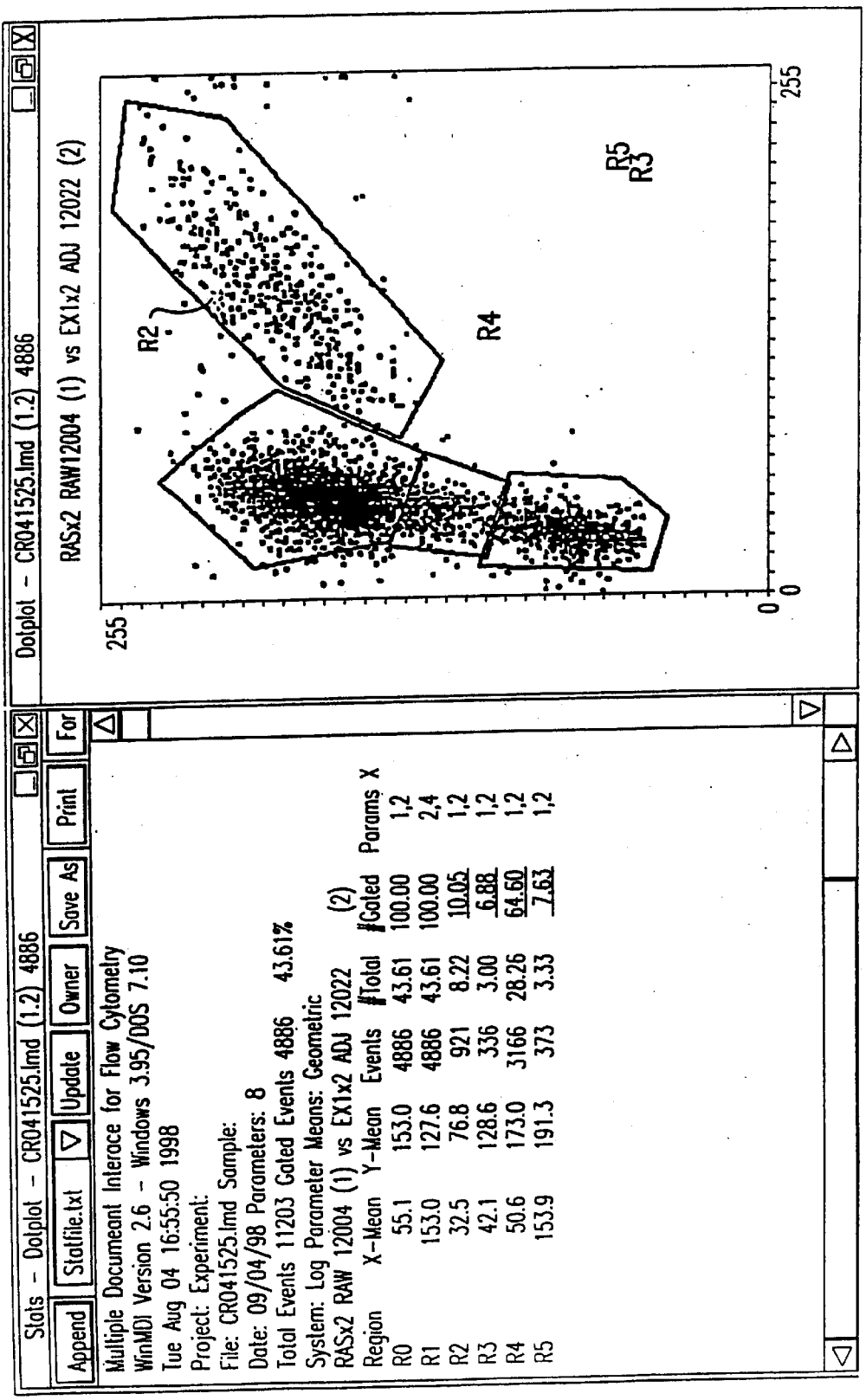
FIG. 7A is a graphical representation of 8% canine eosinophil data employing the prior art.
Figure 7B:
FIG. 7B is a graphical representation of 8% canine eosinophil data employing the present invention.
Figure 8A:
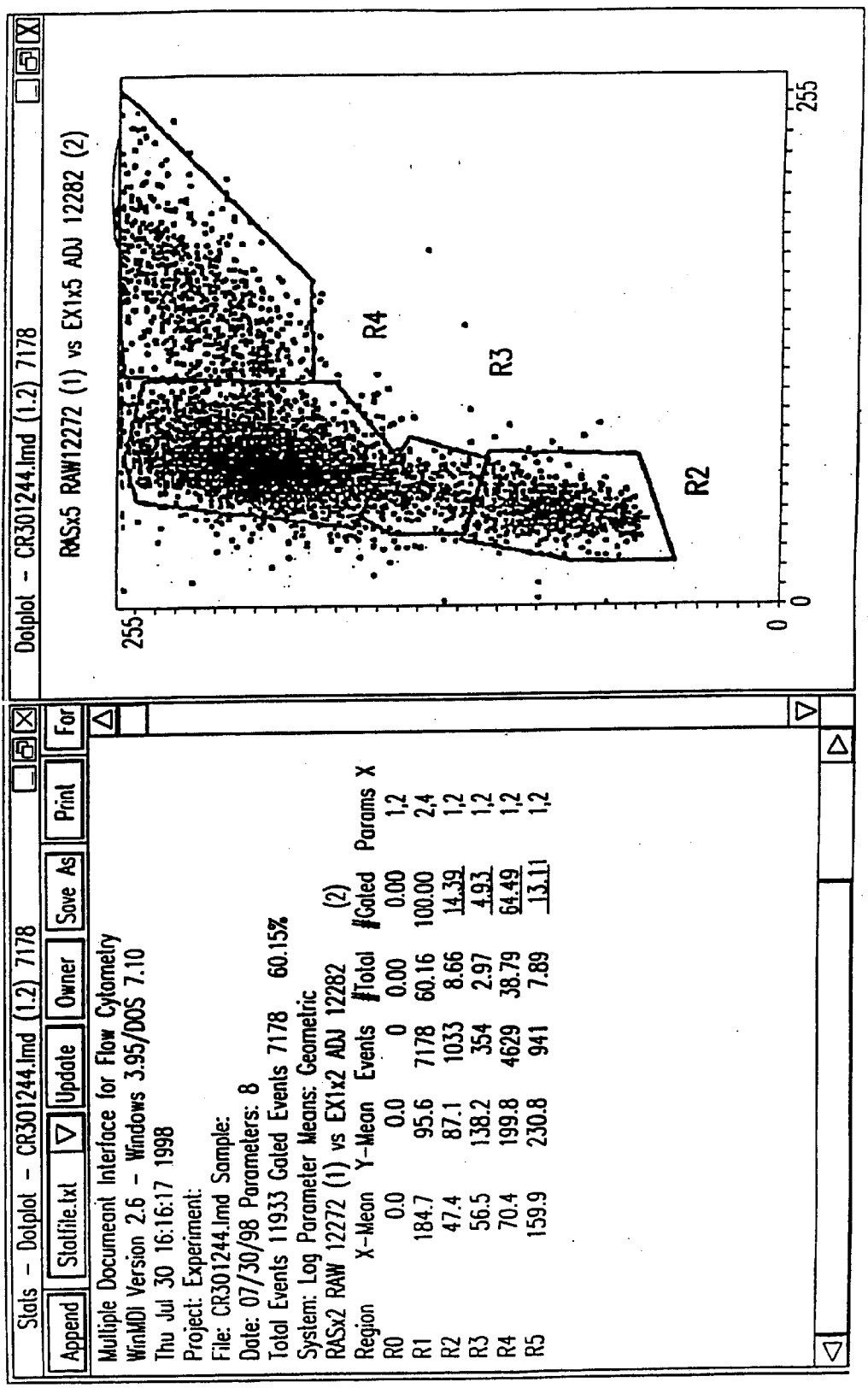
FIG. 8A is a graphical representation of 10% canine eosinophil data employing the prior art.
Figure 8B:
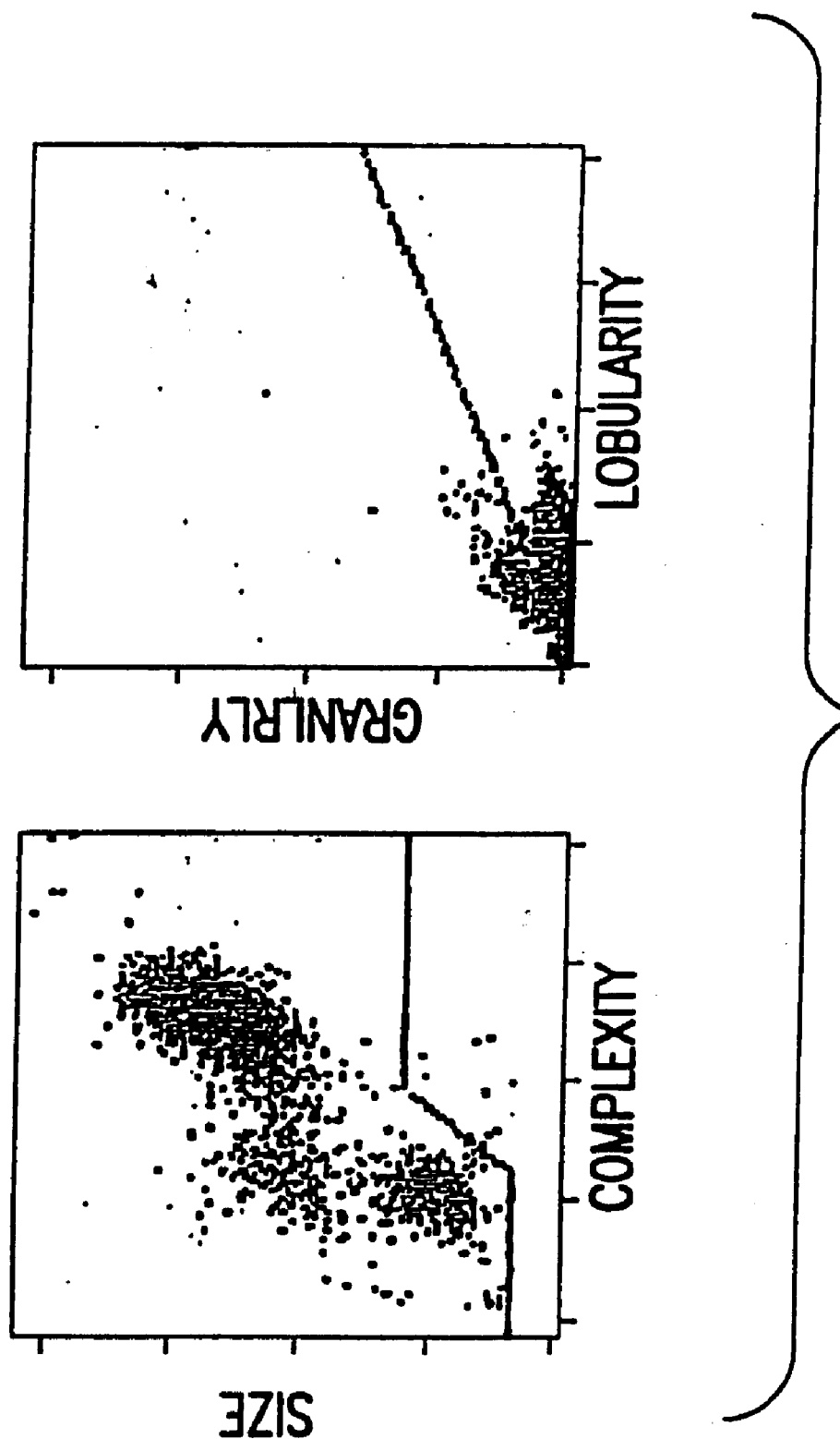
FIG. 8B is a graphical representation of 10% canine eosinophil data employing the present invention.
Figure 9A:
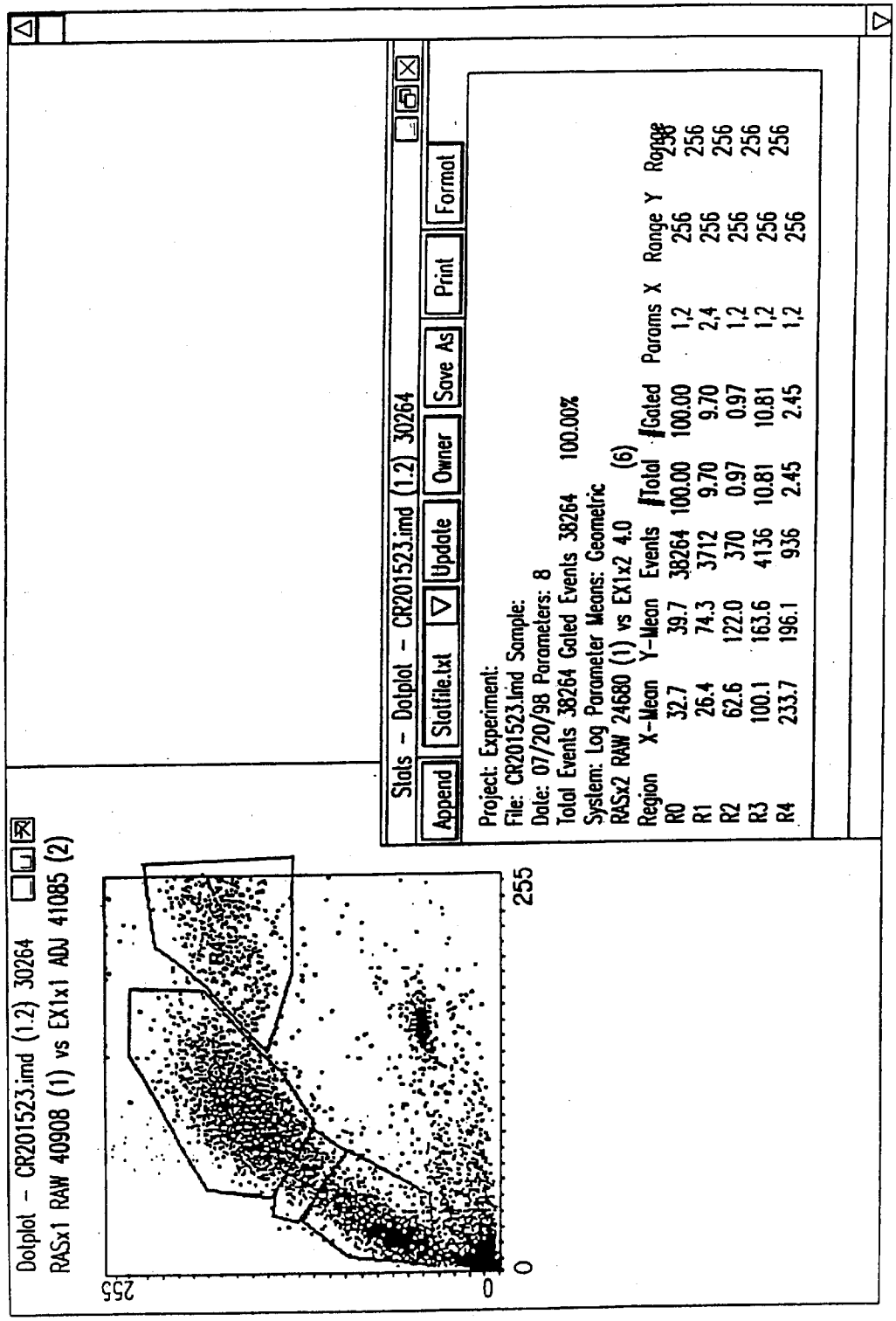
FIG. 9A is a graphical representation of human eosinophil data employing the prior art.
Figure 9B:
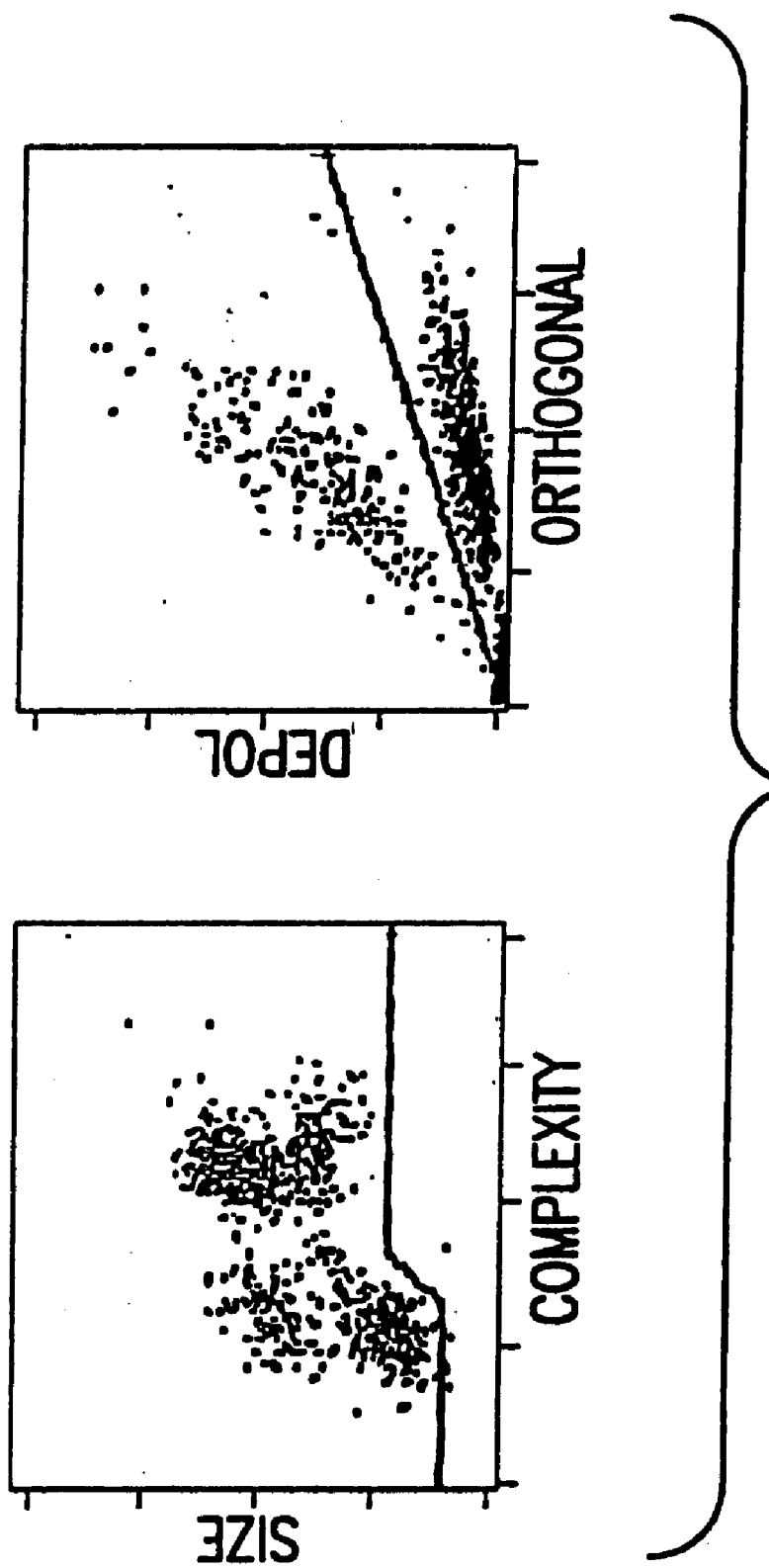
FIG. 9B is a graphical representation of human eosinophil data employing the present invention.

Referring to FIG. 5, the output of the data from the flow cytometer of the present invention is shown. FIG. 5 has the output of right angle scatter light detector 22 as one axis and the output of low angle forward scatter light detector 24 as the other axis. Eosinophils are located to the right of the software threshold line and, as shown in FIGS. 6A, 7A, 8A, and 9A, produce cluster points that are less concentrated than are those of the prior art. Computer software programs employed to identify clusters based on cluster points can thus do so more reliably with the present invention.

Next referring to FIGS. 6A, 6B, 7A, 7A, 7B, 8A, 8B, 9A and 9B, graphical representations of leukocyte identification is shown, with specific reference to eosinophil identification. The data of FIGS. 6A, 7A, 8A, and 9A was employed using the apparatus of the present invention. In FIGS. 6A, 7A, 8A, and 9A the term R2 denotes primarily lymphocytes, R3 denotes primarily monocytes, R4 denotes primarily neutrophils and R5 denotes primarily eosinophils. FIGS. 6B, 7B, 8B, and 9B pertain to data employing an apparatus substantially disclosed in U.S. Pat. No. 5,017,497. Whole blood samples of either canine or human blood were prepared as follows before analyzing with the apparatus of present invention or the prior art. The whole blood sample was diluted 10 to 1 in phosphate buffered saline. Then 40 microliters of the phosphate buffered saline treated whole blood sample was mixed with 1,200 microliters of a lysing solution. The lysing solution consisted of 8.3 grams of ammonium chloride, 1 gram of potassium bicarbonate, 0.37 grams tetrasodium EDTA per liter of lysing solution. The whole blood sample was lysed for 20 minutes to one-half of an hour. It will be readily understood by those skilled in the art that lyse time can readily be reduced to between 30 seconds and one minute.

A good correlation exists between the eosinophil of the present invention of FIGS. 6A, 7A, 8A and 9A with the eosinophil data of the DEPOL/ORTHOGONAL graphical representation of the prior art as shown in FIGS. 6B, 7B, 8B and 9B. More specifically, regarding FIGS. 6A and 6B, the eosinophil value for the present invention is 2.1% and for the prior art is 2.0%. Regarding FIGS. 7A and 7B, the eosinophil data for the present invention is 7.6% and for the prior art is 8.2%. Regarding FIGS. 8A and 8B the eosinophil data for the present invention is 13.1% and for the prior art is 9.8%. Regarding FIGS. 9A and 9B the eosinophil data for the present invention is 10.8% and for the prior art is 14.6%. For all of the above graphical representations of the present invention, FIGS. 6A, 7A, 8A and 9A an eosinophil cluster is present at R5. Regarding the prior art data of FIGS. 6B, 7B and 8B the SIZE/COMPLEXITY graphical representation shows no eosinophil cluster, while the graphical representation of FIG. 9B does show a cluster.

A comparison of the data of the present invention from FIGS. 6A, 7A, 8A and 9A with the prior art data of FIGS. 6B, 7B, 8B and 9B show a marked decreased density or concentration of the cluster points within the eosinophil clusters. The separation of these cluster points allows the software programs that locate and identify different clusters to more readily locate and identify the clusters produced by the apparatus and method of the present invention compared to those of the prior art.

While the invention has been described with reference to particular embodiments and applications, it will be appreciated that various embodiments and applications based on the teaching of the present invention are possible.

What is claimed is:

1. A high numerical aperture flow cytometer, comprising:
   a flow cell;
   a laser input, said laser input emitting a beam of light that is oriented substantially orthogonally to a direction of flow of blood cells through said flow cell;
   a right angle scatter light detector, said right angle scatter light detector being effective to collect a cone of unfiltered right angle scattered light of at least 58° and convert said right angle scattered light into a right angle scattered light signal; and
   a signal processor, said signal processor being effective to distinguish eosinophils from other leukocytes on the basis of said right angle scattered light signal.

2. The high numerical aperture flow cytometer of claim 1, wherein said right angle scatter light detector is located at a distance of about 2 millimeters from said flow cell.

3. The high numerical aperture flow cytometer of claim 1, further comprising at least one low angle forward scatter light detector, said low angle forward scatter light detector being effective to collect low angle forward scattered light at an angle between about 2° to about 5° from said beam.

4. The high numerical aperture flow cytometer of claim 1, wherein said right angle scatter light detector is effective to collect a cone of right angle scattered light of at least 130°.

5. The high numerical aperture flow cytometer of claim 1, further comprising:
   a first forward scatter light detector, said first forward scatter light detector being effective to collect low angle forward scattered light at an angle between about 1° to about 3° from said beam;
   a second forward scatter light detector, said second forward scatter light detector being effective to collect low angle forward scattered light at an angle between about 9° to about 12°;
   an axial light loss detector; and
   a right angle scatter light detector located at a distance of about 2 millimeters from said flow cell and effective to collect a cone of right angle scattered light of at least 130°.

6. The high numerical aperture flow cytometer of claim 1, further comprising:
   a low angle forward scatter light detector, said low angle forward scatter light detector being effective to collect low angle forward scattered light at an angle between about 1° to about 3° from said beam; and
   a right angle scatter light detector located at a distance of about 2 millimeters from said flow cell and effective to collect a cone of right angle scattered light of at least 130°.

7. The high numerical aperture flow cytometer of claim 1, further comprising:
   a low angle forward scatter light detector, said low angle forward scatter light detector being effective to collect low angle forward scattered light at an angle between about 9° to about 12° from said beam; and
   a right angle scatter light detector located at a distance of about 2 millimeters from said flow cell and effective to collect a cone of right angle scattered light of at least 130°.

8. The high numerical aperture flow cytometer of claim 1, further comprising:
   an axial light loss detector; and
   a right angle scatter light detector located at a distance of about 2 millimeters from said flow cell and effective to collect a cone of right angle scattered light of at least 130°.

9. A method for particle discrimination by light scattering, comprising the steps of:
   flowing a fluid containing biological cells through a flow cell;
   directing a beam of light in a direction that contacts said biological cells in said flow cell and is substantially orthogonal to a direction of flow of said biological cells through said flow cell; and
   detecting a cone of unfiltered right angle scattered light of at least 58°;
   converting said detected unfiltered right angle scattered light into a right angle scattered light signal; and
   identifying eosinophils present among said biological cells on the basis of said right angle scattered light signal.

10. The method of claim 9, wherein said step of detecting is performed by a right angle scatter light detector located at a distance of about 2 millimeters from said flow cell.

11. The method of claim 9, further comprising collecting low angle forward scattered light at an angle between about 1° to about 3° from said beam of laser light.

12. The method of claim 9, further comprising collecting low angle forward scattered light at an angle between about 9° to about 12° from said beam of laser light.

13. The method of claim 9, further comprising collecting axial light loss from said beam of laser light.

14. The method of claim 9, further comprising detecting a cone of right angle scattered light of at least 130°.

15. The method of claim 9, further comprising:

detecting said cone of right angle scattered light by using a right angle scatter light detector located at a distance of about 2 millimeters from said flow cell;

collecting low angle forward scattered light at an angle between about 1° to about 3° from said beam of laser light collecting forward scattered light at an angle between about 9° and about 12° measuring axial light loss; and detecting a cone of right angle scattered light of at least 130°.

* * * * *

UNITED STATES PATENT AND TRADEMARK OFFICE
CERTIFICATE OF CORRECTION

PATENT NO. : 6,618,143 B2
DATED : September 9, 2003
INVENTOR(S) : Roche et al.

Figure 1:
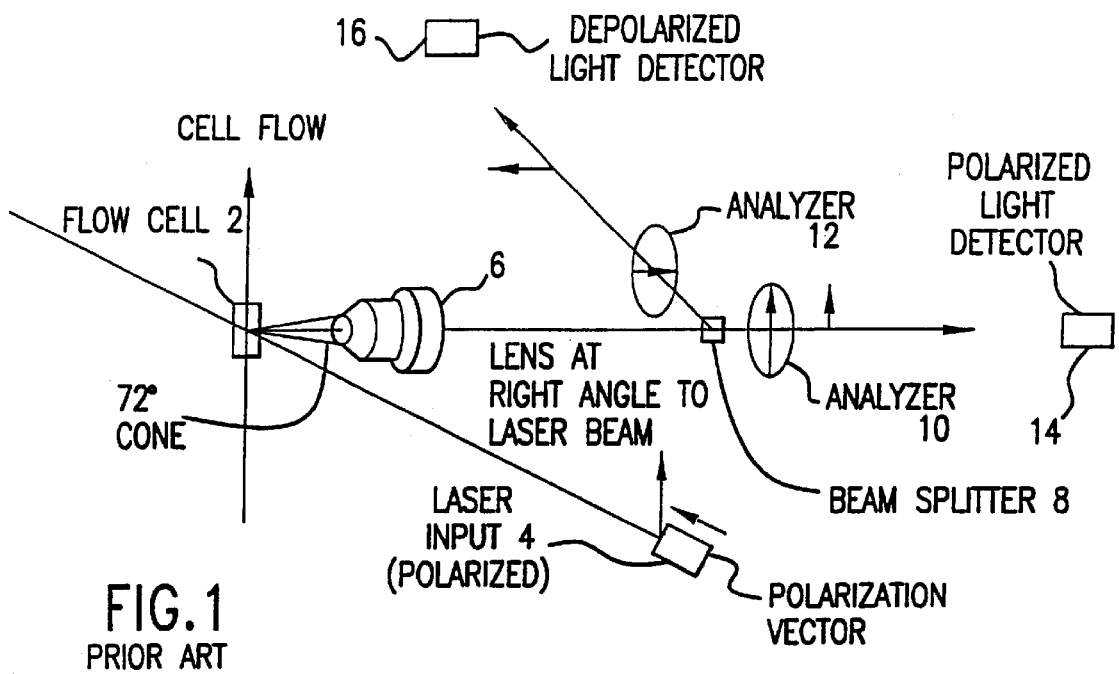
FIG. 1 is a schematic representation of the electro-optical components of prior art.

It is certified that error appears in the above-identified patent and that said Letters Patent is hereby corrected as shown below:

Column 1,
Line 7, "U.S. Pat. No. 6,320,656, the entire text and figures of which are hereby incorporated by reference." should read -- U.S. Pat. No. 6,320,656, which claims the benefit of U.S. Provisional Patent Application Serial No. 60/120,804, filed February 19, 1999, the entire text and figures of which are hereby incorporated by reference. --.
Line 28, after "de Grooth et al.", insert -- FIG. 1 of the present application illustrates the apparatus disclosed in the '497 patent. --

Column 2,
Line 4, "the axis." should read -- the other axis. --.

Column 3,
Line 11, "input" should read -- input. --.

Column 4,
Lines 17, 22, 26 and 30, "the prior art" should read -- the present invention --.
Lines 19, 24, 28 and 32, "the present invention" should read -- the prior art --.

Column 5,
Line 13, "manometer" should read -- nanometer --.
Line 65, "Indications form" should read -- Indications from --.

Column 6,
Line 57, "Next referring to FIGS. 6A, 6B, 7A, 7A, 7B, 8A, 8B, 9A" should read -- Next referring to FIGS. 6A, 6B, 7A, 7B, 8A, 8B, 9A --.

UNITED STATES PATENT AND TRADEMARK OFFICE
CERTIFICATE OF CORRECTION

PATENT NO.   : 6,618,143 B2
DATED         : September 9, 2003
INVENTOR(S)  : Roche et al.

It is certified that error appears in the above-identified patent and that said Letters Patent is hereby corrected as shown below:

Column 7,
Line 12, "between the eosinophil of the" should read -- between the eosinophil data of the --.

Signed and Sealed this

Twenty-second Day of June, 2004

JON W. DUDAS
*Acting Director of the United States Patent and Trademark Office*